US011246751B2

(12) United States Patent
Orloff et al.

(10) Patent No.: US 11,246,751 B2
(45) Date of Patent: Feb. 15, 2022

(54) DISPENSING DEVICES AND METHODS

(71) Applicant: Orloff Eye Group, Inc., Bayside, NY (US)

(72) Inventors: Eugene Orloff, Bayside, NY (US); Eleonora Orloff, Bayside, NY (US); Jeremy Irons, Los Angeles, CA (US); Robert L. Marvin, Jr., Plainville, CT (US)

(73) Assignee: Orloff Eye Group, Inc., Bayside, NY (US)

( * ) Notice: Subject to any disclaimer, the term of this patent is extended or adjusted under 35 U.S.C. 154(b) by 323 days.

(21) Appl. No.: 15/276,276

(22) Filed: Sep. 26, 2016

(65) Prior Publication Data

US 2017/0266043 A1    Sep. 21, 2017

Related U.S. Application Data

(60) Provisional application No. 62/309,622, filed on Mar. 17, 2016.

(51) Int. Cl.
*A61F 9/00* (2006.01)

(52) U.S. Cl.
CPC .................... *A61F 9/0026* (2013.01)

(58) Field of Classification Search
CPC ........................................... A61F 9/0026
See application file for complete search history.

(56) References Cited

U.S. PATENT DOCUMENTS

| 2,722,216 A | 11/1955 | Robbins |
| 3,521,636 A | 7/1970 | Mahoney et al. |
| 4,002,168 A * | 1/1977 | Petterson ............. B65D 23/003 604/298 |

(Continued)

FOREIGN PATENT DOCUMENTS

| WO | WO 1996019177 | 6/1996 |
| WO | WO 2012072546 A1 | 6/2012 |

OTHER PUBLICATIONS

Nahanee, Morgan, Glasses and Your Nose: Getting the Right Bridge Fit, Jul. 3, 2015, Retrieved from the Internet Apr. 9, 2017, https://www.spectacleshoppe.ca/blogs/news/34875972-glasses-and-your-nose-getting-the-right-bridge-fit>; third paragraph.

(Continued)

*Primary Examiner* — Catharine L Anderson
*Assistant Examiner* — Arjuna P Chatrathi
(74) *Attorney, Agent, or Firm* — Kramer Levin Naftalis & Frankel LLP

(57) ABSTRACT

Disclosed herein are improved dispensing devices for facilitating application of eye drops that are ergonomic, promote improved patient adherence, and eliminate the need for extraneous gadgets or facilitating devices that may add additional expense to users. A dispensing device can include a container body for storing drops and a nozzle coupled to the body for dispensing the drops. The device can include one or more channels defined on a surface of the container body and configured to couple, or otherwise mount or abut, to an anatomical structure of a user (such as, for example, a user's nose bridge or eyebrow ridge). The device can also include one or more grip areas defined on the container body and configured to allow a user to generally hold the device and to apply force thereto to dispense drops from the device.

18 Claims, 14 Drawing Sheets

(56) References Cited

U.S. PATENT DOCUMENTS

| | | | |
|---|---|---|---|
| 4,257,417 A | 3/1981 | Gibilisco | |
| 4,392,590 A * | 7/1983 | Hofmann-Igl | A61F 9/0026 222/174 |
| 5,255,024 A | 10/1993 | Jensen | |
| 5,648,084 A | 7/1997 | Guttag | |
| 6,161,713 A | 12/2000 | Krich | |
| 6,371,945 B1 | 4/2002 | Sherman | |
| 6,595,970 B1 * | 7/2003 | Davidian | A61F 9/0026 604/298 |
| 6,632,202 B1 | 10/2003 | Hagele | |
| 7,325,708 B2 | 2/2008 | Barber | |
| 8,206,362 B1 | 6/2012 | Crosswell, Jr. | |
| 8,348,912 B2 | 1/2013 | Rehkemper et al. | |
| 2009/0182291 A1 * | 7/2009 | Eilat | A61F 9/0026 604/290 |
| 2009/0207373 A1 | 8/2009 | Stinson | |
| 2011/0118678 A1 * | 5/2011 | Rehkemper | A61F 9/0026 604/290 |
| 2012/0150132 A1 * | 6/2012 | Cress | A61F 9/0026 604/290 |
| 2015/0313757 A1 * | 11/2015 | Agnew | A61F 9/0008 604/521 |
| 2016/0038339 A1 * | 2/2016 | Behan | A61F 9/0026 604/290 |

OTHER PUBLICATIONS

International Search Report Application No. PCT/2017/16645, International Filing Date Feb. 6, 2017, dated May 8, 2017.
Eye Drop Dispenser, Eye Drop Device, Eye Drop Guide, https://ezdrops.com/, dated Nov. 23, 2015.
E-Z Drops? Dry Eye Relief, Glaucoma, Eye Infection, http://www.ezdrops.com/ez-drops-product.html, dated Nov. 23, 2015.

* cited by examiner

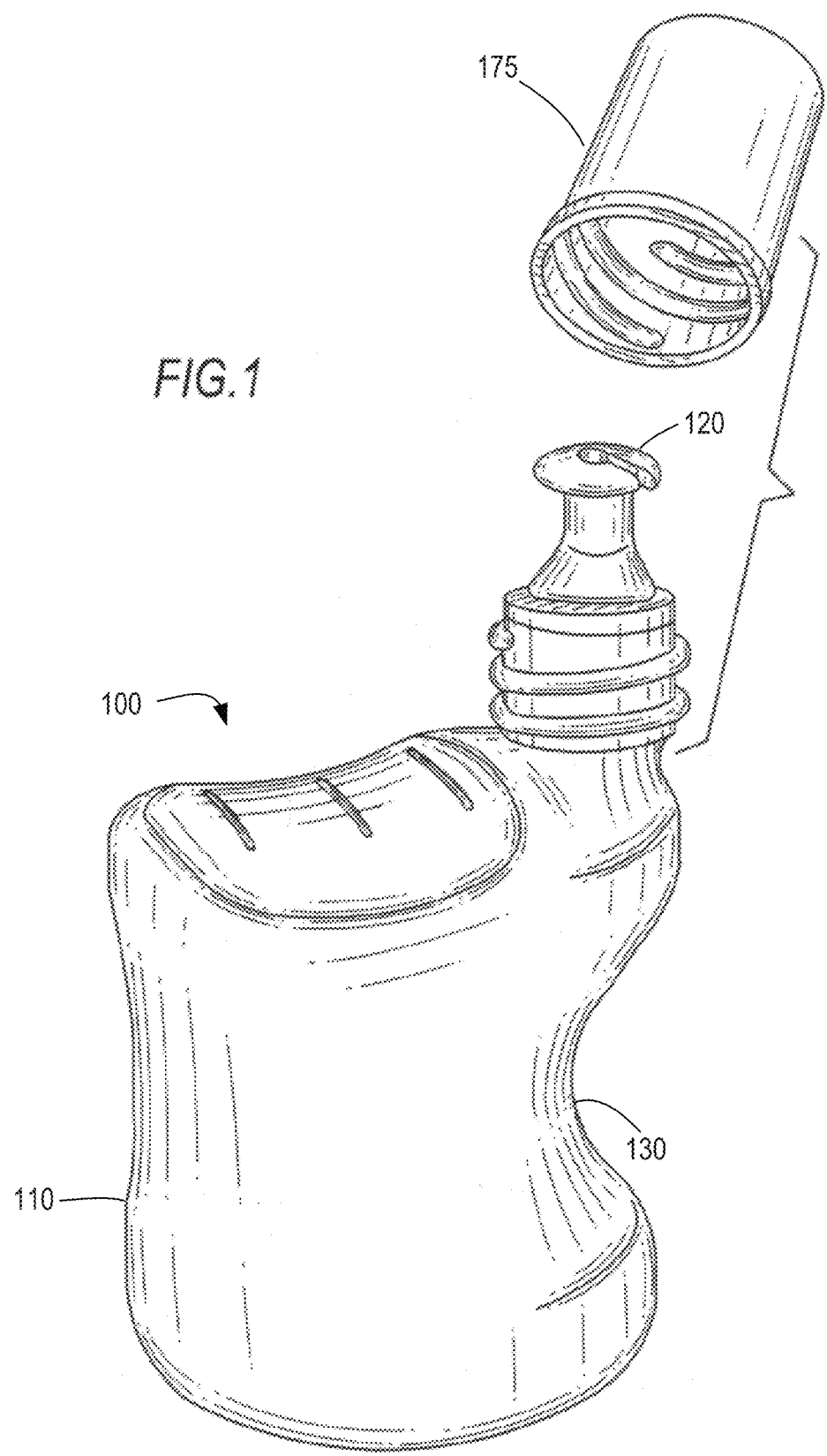

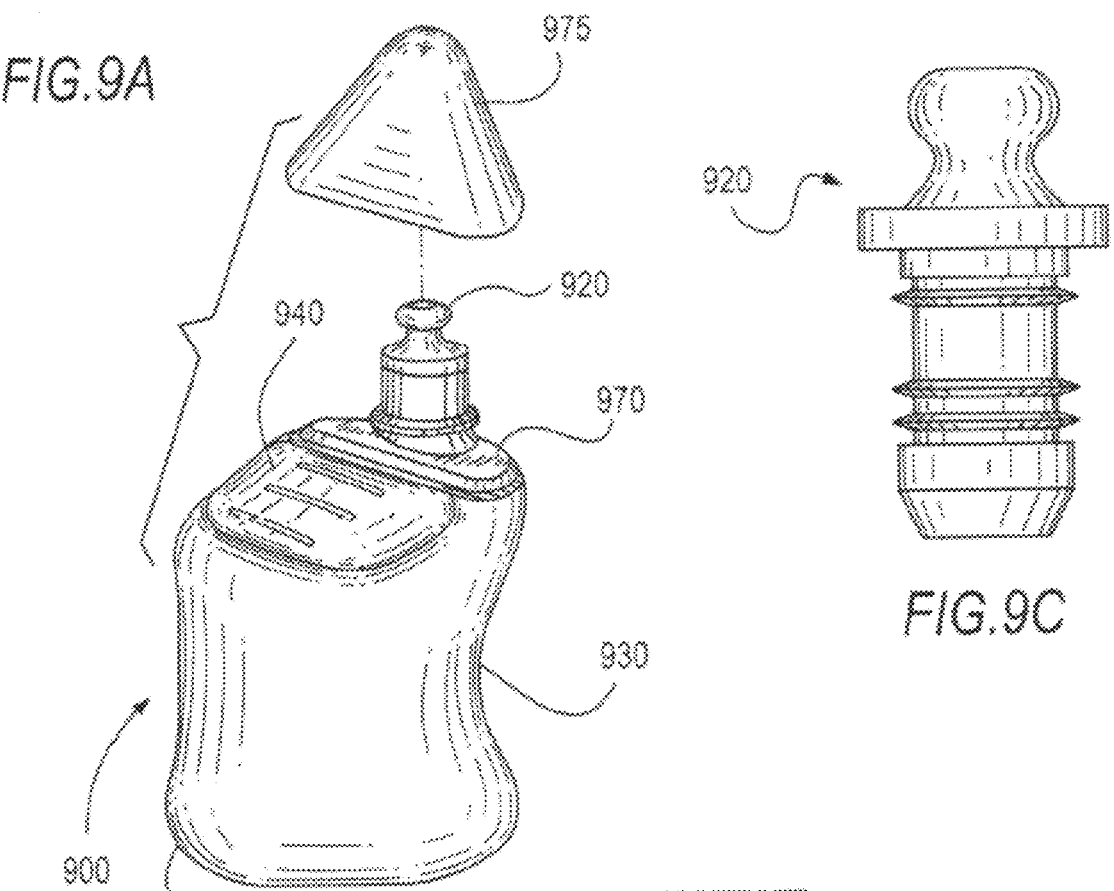
FIG.9A
FIG.9C
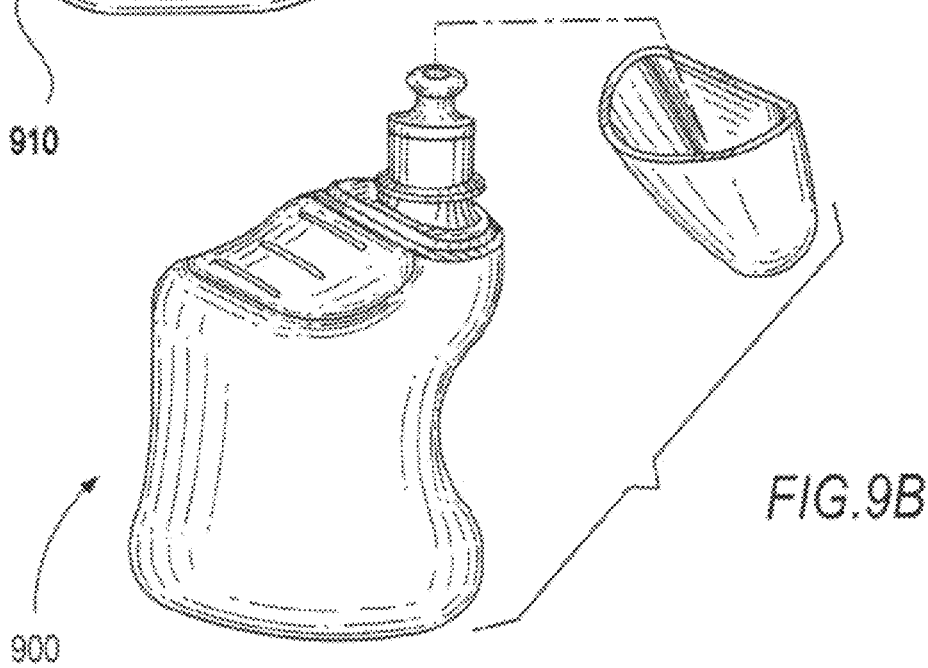
FIG.9B

DISPENSING DEVICES AND METHODS

CROSS-REFERENCE TO RELATED PROVISIONAL APPLICATION

This application claims the benefit of U.S. Provisional Patent Application No. 62/309,622, filed on Mar. 17, 2016, the disclosure of which is hereby incorporated herein by reference in its entirety.

FIELD OF THE INVENTION

The present invention generally relates to devices and methods for dispensing drops, and more particularly eye drops, whether in fluid (e.g., liquid), gel, or paste form (hereinafter referred to simply as drops or eye drops).

BACKGROUND OF THE INVENTION

Eye drops have traditionally been stored and dispensed using bottles or single dose containers (such as UniDose® containers). These are typically constructed of resilient materials, which allows users to squeeze, or otherwise compress, the containers to apply the drops to their eyes. Users of drops may have difficulty applying drops from conventional containers, which require positioning the bottles and nozzles over their eyes and squeezing. This can be especially problematic for older users or those with medical conditions (such as arthritis, tremors, or Parkinson's disease), who often find it difficult to steady their hands during drop dispensing or may have problems gripping and squeezing. Even when standing in front of a mirror, these users frequently miss their eyes (which leads to waste, especially if the drops are expensive). It may also be difficult for visually-impaired patients to see the bottle. Indeed, these can be serious problems for those who need to apply eye drops multiple times a day, and can generally result in poor patient adherence with prescribed drug regimens.

Various contraptions have been proposed in the past to address this issue. These included frames or other gadgets configured to rest on a portion of the user's face (e.g., the nose, cheeks, or area beneath the eyes) and to receive and position the bottle near the eye so that the user can apply the drops without having to hold the bottle. One problem with these contraptions is that they are extraneous components that users have to keep handy with their eye drop bottles. For each new bottle, for example, the contraption must be removed from the old bottle and attached or applied to the new one, which can require extra steps and effort on the part of the consumer. Since these contraptions are separate from the bottles, they can represent an additional expense and can also be easily lost or misplaced. Moreover, some of these gadgets also retain the bottle nozzle fairly close to the eye, which can cause abrasions or other injuries to the eye if the contraption is accidentally shifted or moved during drop application.

There is thus a need for eye drop dispensing devices that address the disadvantages of conventional bottles and solutions.

BRIEF SUMMARY OF THE INVENTION

Generally speaking, it is an object of the present invention to provide improved devices and methods for dispensing eye drops, and more particularly, improved bottles for facilitating the application of eye drops that are ergonomic, promote improved patient adherence, and eliminate the need for extraneous gadgets or facilitating devices that may add additional expense to users.

According to various embodiments, a dispensing device can include a container body for storing drops and a nozzle coupled to the body for dispensing the drops. The device can include one or more channels defined on a surface of the container body and configured to couple, or otherwise mount or abut, to an anatomical structure of a user (such as, for example, a user's nose bridge or eyebrow ridge). The device can also include one or more grip areas defined on the container body and configured to allow a user to generally hold the device and to apply force thereto to dispense drops from the device.

According to some embodiments, a method for dispensing drops from a dispensing device is provided. The dispensing device includes a container body configured to store drops, and has a nozzle coupled to the container body, and a channel and at least one grip area defined on the container body. While the container body is disposed such that the channel couples, mounts, or abuts to a user's nose bridge or eyebrow ridge, the method includes at least partially compressing the container body and dispensing the drops via the nozzle when an external force is exerted on the at least one grip area. When the external force is no longer exerted on the at least one grip area, the method includes returning the container body to its uncompressed state and halting dispensing of the drops.

BRIEF DESCRIPTION OF THE DRAWINGS

The present invention is discussed in greater detail below with reference to exemplary embodiments illustrated in the accompanying drawings, in which:

FIG. 1 is a perspective view of an exemplary dispensing device, in accordance with various embodiments of the present invention;

FIGS. 9A and 9B are various views of an exemplary dispensing device having a removable cap, in accordance with various embodiments of the present invention;

FIG. 9C is a front view of a nozzle of the dispensing device of FIGS. 9A and 9B, in accordance with various embodiments of the present invention;

DETAILED DESCRIPTION

Figure 2A:
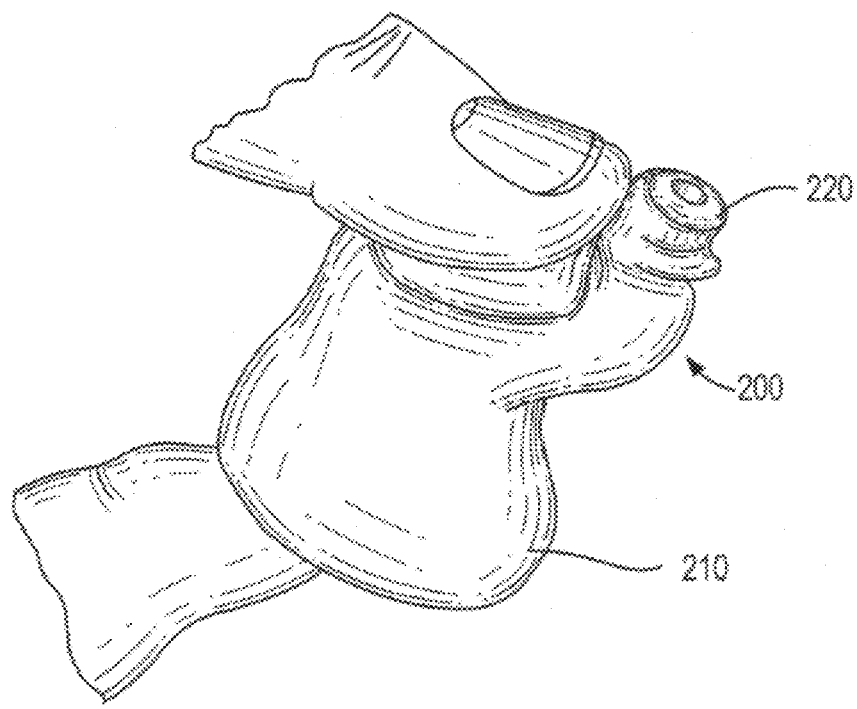
FIG. 2A is a perspective view of an exemplary dispensing device in its natural, defined state, in accordance with various embodiments of the present invention.

Referring to the drawing figures, FIG. 1 is a perspective view of an exemplary eye drop dispensing device 100. Dispensing device 100 includes a container body 110 for storing drops and a nozzle 120 coupled to the body for dispensing the drops. Dispensing device 100, and more particularly, container body 110 can be composed of any material suitable for storing eye drops. For example, container body 110 can be composed of plastics, such as synthetic resins, acrylic, doped acrylic, polyacrylic—e.g., PMMA, elastomers, or the like—polyethylene (PE), polypropylene (PP), and/or high density polyethylene (HDPE). In preferred embodiments, the material can be squeezable, elastic, or otherwise compressible, so as to allow dispensing of the drops therefrom when appropriate force is applied to the device.

Figure 2B:
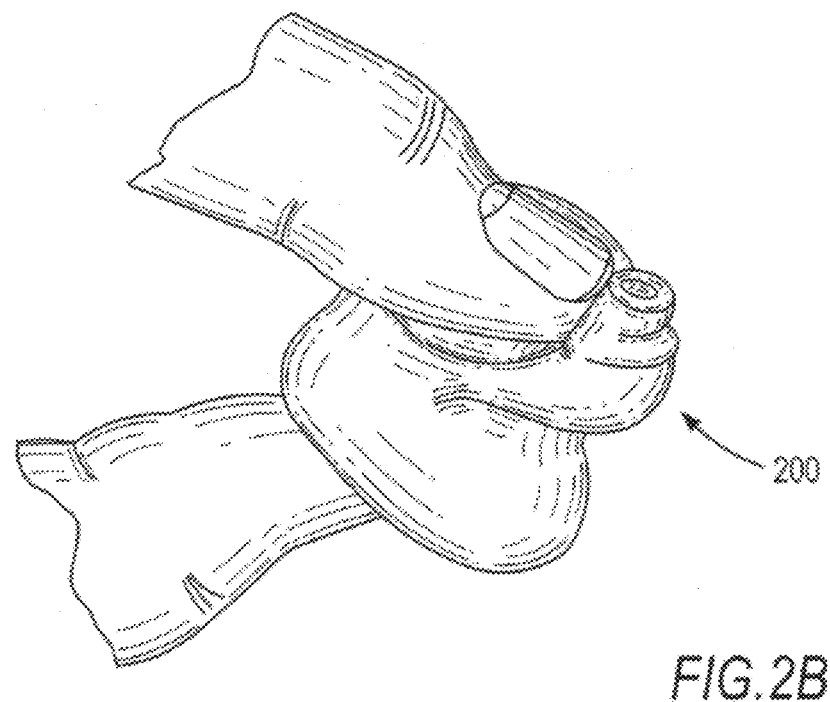
FIG. 2B is a perspective view of the dispensing device of FIG. 2A in a compressed state, in accordance with various embodiments of the present invention.
Figure 12A:
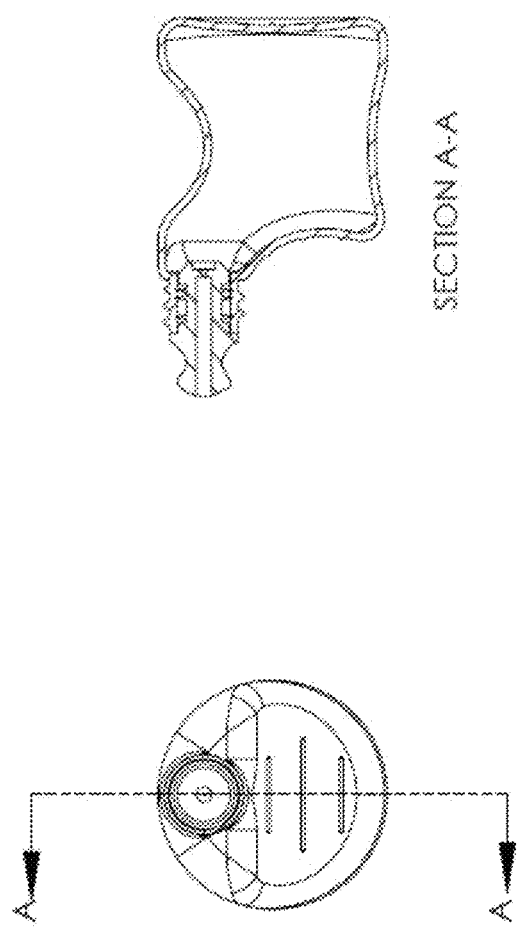
FIGS. 12A-12C are views of an exemplary dispensing device, depicting various dimensions of the device in accordance with certain embodiments of the present invention.

In certain embodiments, one or more properties of the material (including, for example, the thickness thereof) can be adjusted to control the overall compressibility and resilience of the container body. The container body can have any suitable thickness. In some embodiments, the thickness of the container body can be between 0.1 and 2 millimeters, such as, for example, about 0.5 millimeter or about 0.7 millimeter (see, e.g., FIG. 12A). FIG. 2A is a perspective view of a dispensing device 200 (which may be similar to dispensing device 100, and which can include a container body 210 and a nozzle 220) in its natural, defined state. FIG. 2B is a perspective view of dispensing device 200 in a compressed state. The properties of the material can be adjusted using any suitable method, including, for example, one or more of grooving, billowing, and fissuring. This can optimize the container body for efficient dispensing of drops during use (e.g., as shown in FIG. 2B), while also allowing the body to return to its natural, defined state and shape after use (e.g., as shown in FIG. 2A).

Figure 12B:
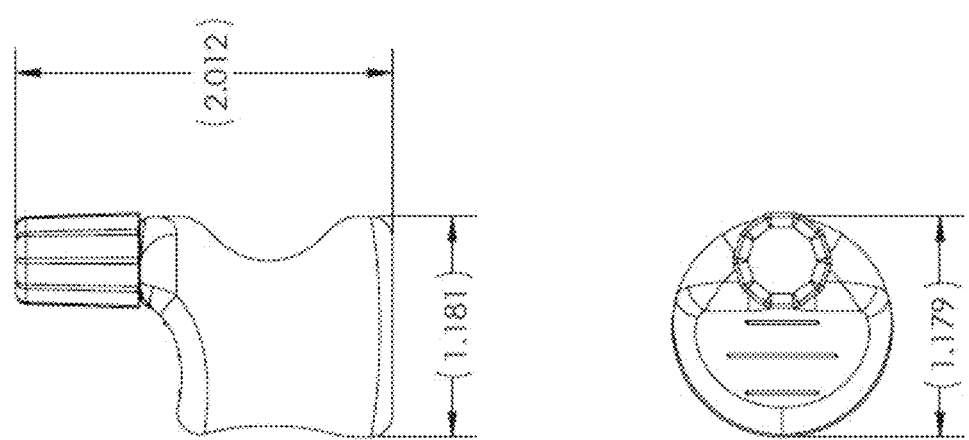
Figure 12C:
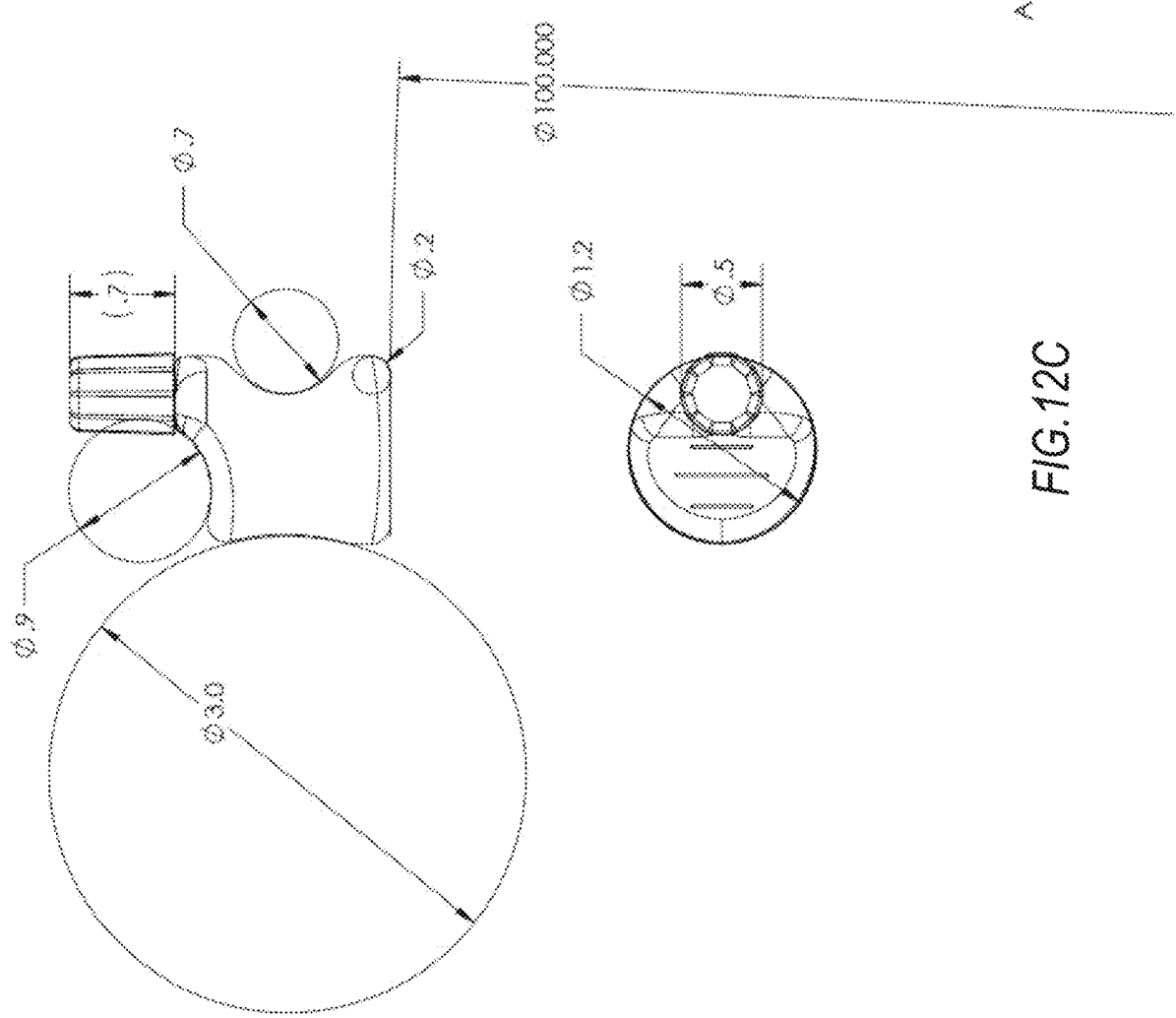

It is to be appreciated that the size of the dispensing device can be defined to store any suitable amount of drops (e.g., 1 milliliter, 2.5 milliliters, 5 milliliters, 7.5 milliliters, 10 milliliters, 15 milliliters, or 30 milliliters). Additionally, the container body and a cap (e.g., cap 175) therefor can have any suitable height and diameter/width. In some embodiments, the height of the container body (e.g., from its bottom surface to either the tip of the nozzle or to the upper surface of the cap disposed about the nozzle) can be in the range from about 1 and 5 inches, such as, for example, about 2 inches. In various embodiments, the diameter or width of the container body (e.g., across its top surface/portion or bottom surface/portion) can be in the range from about 0.5 and 5 inches, such as, for example, about 1.2 inches. In certain embodiments, the height of the cap can be in the range from about 0.1 and 2 inches, such as for example, about 0.7 inch. In at least one embodiment, the diameter or width of the cap can be in the range from about 0.1 and 2 inches, such as, for example, about 0.5 inch. See, e.g., FIGS. 12B and 12C.

In various embodiments, the dispensing device can include a channel defined on a surface of the container body and configured to couple, or otherwise mount or abut, to an anatomical structure of a user (such as, for example, a user's nose bridge or eyebrow ridge). Referring to FIG. 1, for example, dispensing device 100 can include a channel 130 defined on container body 110, particularly on a side or lateral surface of the container body, adjacent the bottom end or the top portion of the body. Embodiments of the dispensing device will thus be helpful for users to easily orient and position the device over their nose bridge or eyebrow ridge and easily dispense the drops at their eyes without the need to clearly see the dispenser, which is especially important for users who have limited or poor vision, but still require eye drops as treatment. The new bottle design also facilitates the use of drops by negating the need to hold an arm in free space without support, benefiting patients with limited dexterity.

In various embodiments, the dispensing device can also include one or more grip areas defined on the container body for improved ergonomics and ease of grip. One or more designated grip areas on the dispensing device can be configured to receive, for example, one or more of a user's finger(s). In certain embodiments, the grip area(s) can be formed as depression(s) or indentation(s) on the container body. The dispensing device can include a grip area at a top portion of the body adjacent the nozzle (and/or located generally opposite the channel). The dispensing device can additionally, or alternatively, include a grip area at a bottom end of the body. FIGS. 3A-3F are various views of a dispensing device 300 (which may be similar to dispensing devices 100 and 200). Dispensing device 300 can include a container body 310, a nozzle 320, a channel 330, and grip areas 340 and 350. Grip area 340 can be disposed at or proximate the top surface of container body 310 and grip area 350 can be disposed at or proximate the bottom surface of the body. By defining and/or orienting the grip areas in this way, a user can grasp the device with improved ergonomics (e.g., by placing one finger, such as the thumb, on one of the grip areas, and another finger, such as the index or middle finger, on the other grip area) to position the device on an anatomical structure, and to squeeze or compress it to dispense drops. For example, if a user chooses to position the device over the nose bridge or eyebrow ridge, the grip areas advantageously allow the user to hold the device and apply drops to both of the user's eyes using the user's dominant hand and without having to lift the user's fingers off of the grip areas. After applying one or more drops to one eye, the user can, for example, simply rotate the device 180 degrees, while keeping the user's fingers on the grip areas, and apply one or more drops to the other eye. FIGS. 4 and 4A-4D show a variety of ways that a user can grip (e.g., using one or more fingers) and/or position a dispensing device to dispense drops into the user's eyes.

It should be appreciated that the grip areas can be especially useful for squeezing the device and dispensing drops when the device is positioned on a user's nose bridge, rather than the eyebrow ridge. In the latter case, the user can, for example, simply press onto the surface of the container body generally opposite the channel or, alternatively, generally squeeze the sides of the container body to dispense the drops, without having to utilize the grip areas. The container device may be depressed with the palm of the user's hand against the nose bridge or the eyebrow ridge to dispense drops without involving the fingers in the squeezing process, which may be advantageous for patients with limited dexterity and grip strength, such as those with severe arthritis.

Figure 3A:
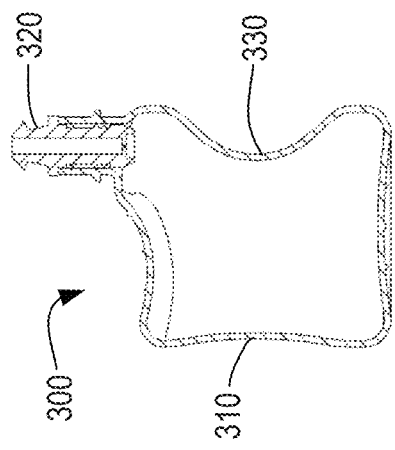
FIGS. 3A-3F are various views of an exemplary dispensing device, in accordance with various embodiments of the present invention.
Figure 3B:
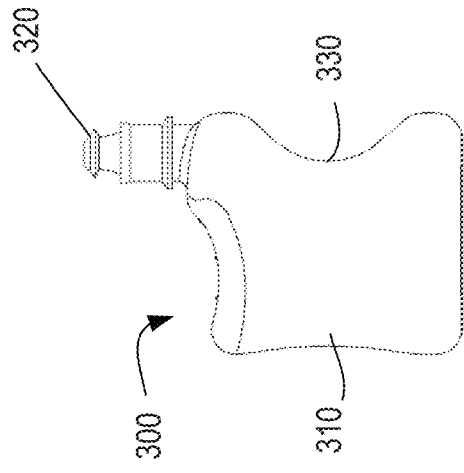
Figure 3C:
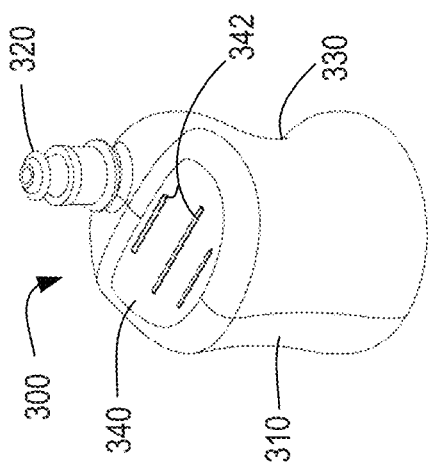
Figure 3D:
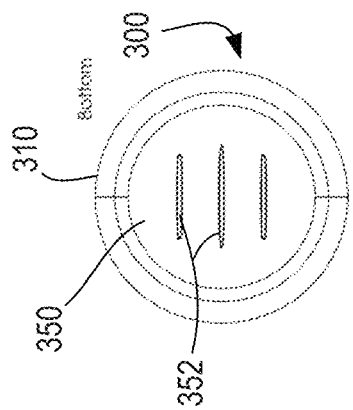
Figure 3E:
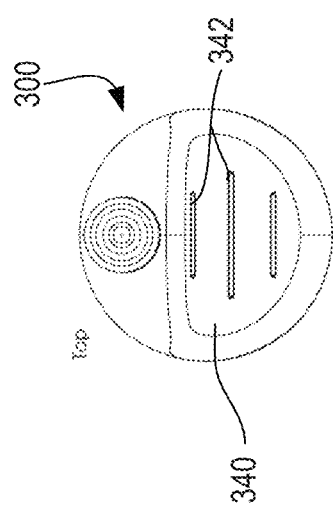
Figure 3F:
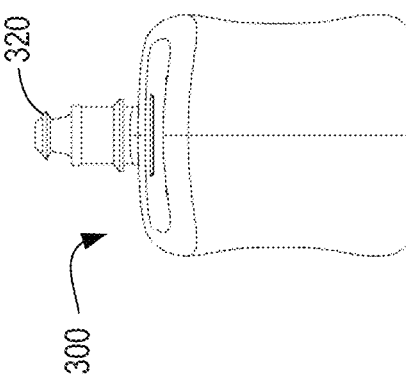
Figure 4:
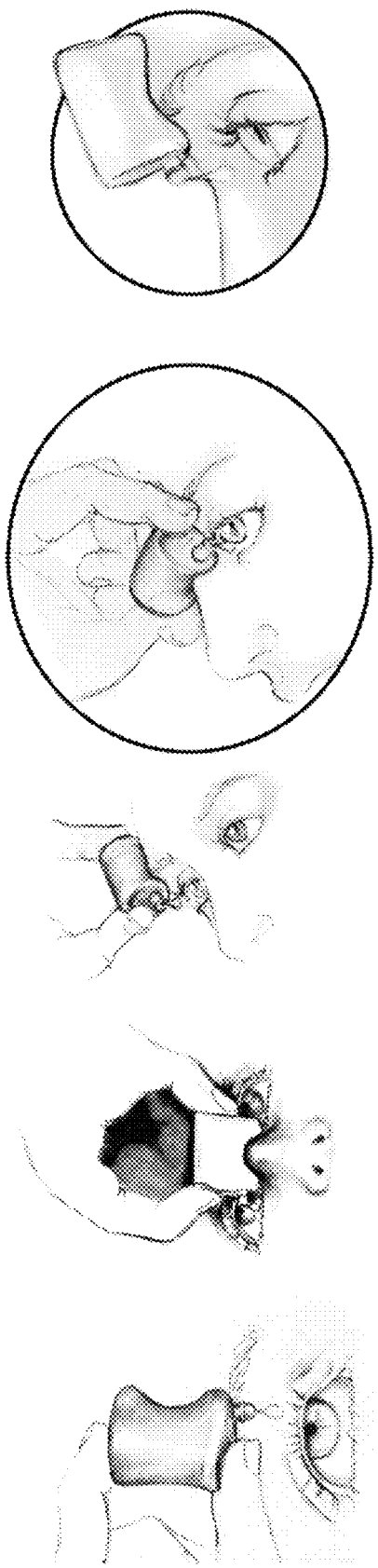
FIGS. 4 and 4A-4D illustrate a variety of ways that a user can grip (e.g., using one or more fingers) and/or position a dispensing device to dispense drops into the user's eyes, in accordance with various embodiments of the present invention.
Figure 4A:
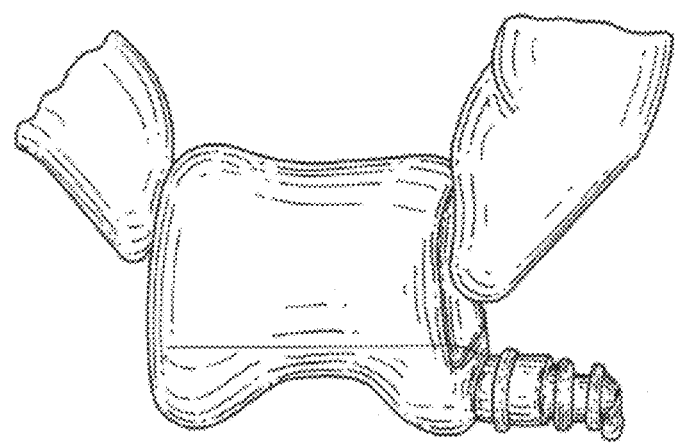
Figure 4B:
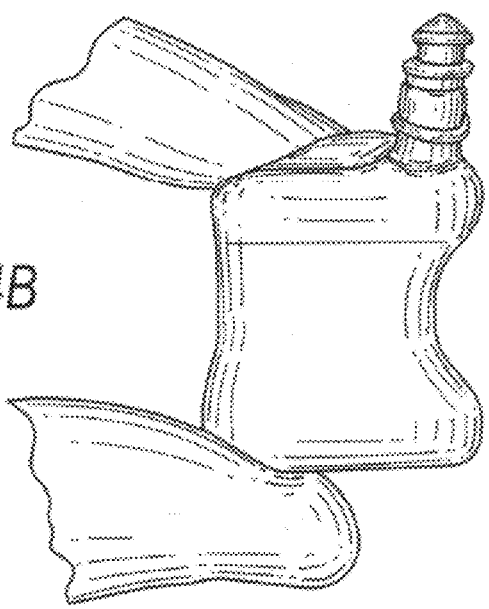
Figure 4C:
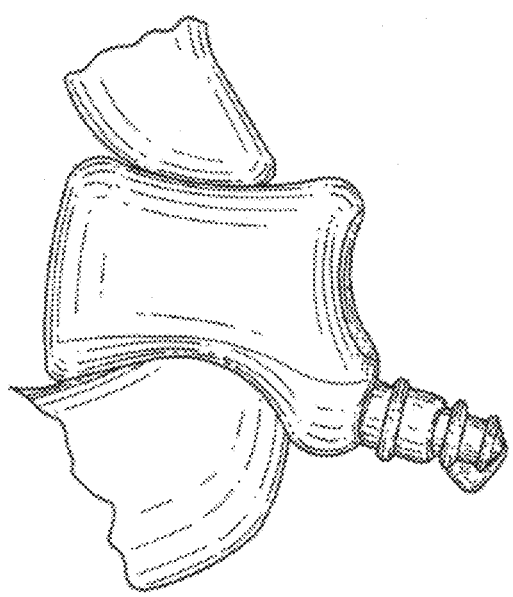
Figure 4D:
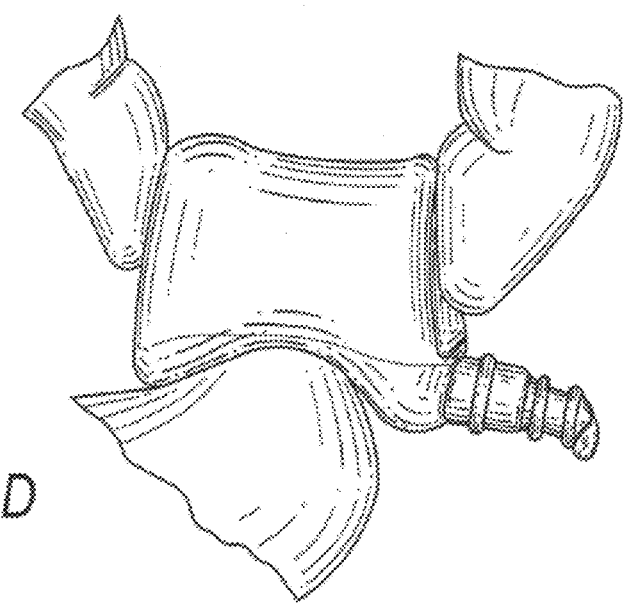

In certain embodiments, one or more of the grip areas can include indentations, depressions, raised portions, grooves, scores, or notches (e.g., features 342 and 352 shown in FIGS. 3A, 3E, and 3F). These can serve as indicators to a user that the areas are intended for user contact (e.g., gripping or other contact using the user's fingers), and can also provide sufficient frictional forces that assist the user in gripping and compressing the dispensing device.

It is to be appreciated that, since the channel and the grip area(s) can be constructed as part of the container body, they can exhibit like compressibility and resilience characteristics as the remainder of the body.

The container body can assume a variety of shapes with different channel and grip area dimensions and curvature characteristics. In certain embodiments, the channel can be generally concave (e.g., having an internal angle greater than 180 degrees). In some embodiments, the concavity of the channel can be selected to correspond to curvature characteristics similar to those defined for nose pads or bridges of eyeglasses. This can optimize coupling, mounting, or abutment of the channel to a user's anatomical structure, such as the nose bridge, during drop dispensing.

Each of the curvatures of the channel (e.g., channel 130), the surface of the container body substantially opposite the channel, the grip areas (e.g., grip areas 340 and 350), the internal end of the concave channel proximate the bottom of the container body (i.e., the bottom concave end) can have any suitable geometrical dimensions. The curvature dimensions of the channel and grip areas can, for example, be selected to accommodate the human anatomy. Curvatures can be modeled by imaginary circles having radii or diameters corresponding to the curvatures. See, e.g., FIG. 12C. In some embodiments, the diameter of an imaginary circle modeling the curvature of the channel can be in the range from about 0.1 and 2 inches, such as, for example, about 0.7 inch. In various embodiments, the diameter of an imaginary circle modeling the curvature of the surface of the container body substantially opposite the channel can be in the range from about 1 inch and 10 inches, such as, for example, about 3 inches. In certain embodiments, the diameter of an imaginary circle modeling the curvature of the upper grip area (e.g., grip area 340) can be in the range from about 0.1 and 2 inches, such as, for example, about 0.9 inch. In at least one embodiment, the diameter of an imaginary circle modeling the curvature of the lower grip area (e.g., grip area 350) or bottom surface of the container body can be in the range from about 50 and 200 inches, such as, for example, about 100 inches. In some embodiments, the diameter of an imaginary circle modeling the curvature of the internal bottom concave end can be in the range from about 0.1 and 1 inch, such as, for example, about 0.2 inch.

Figure 5A:
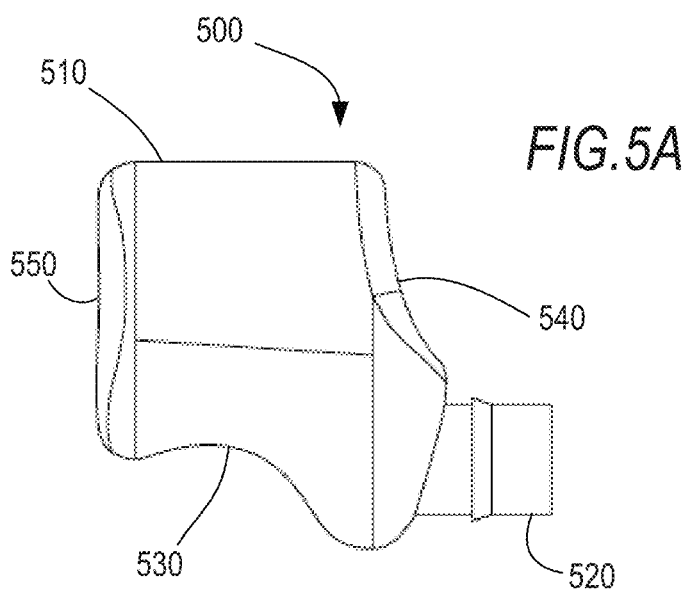
FIGS. 5A and 5B are various views of an exemplary dispensing device, in accordance with various embodiments of the present invention.
Figure 5B:
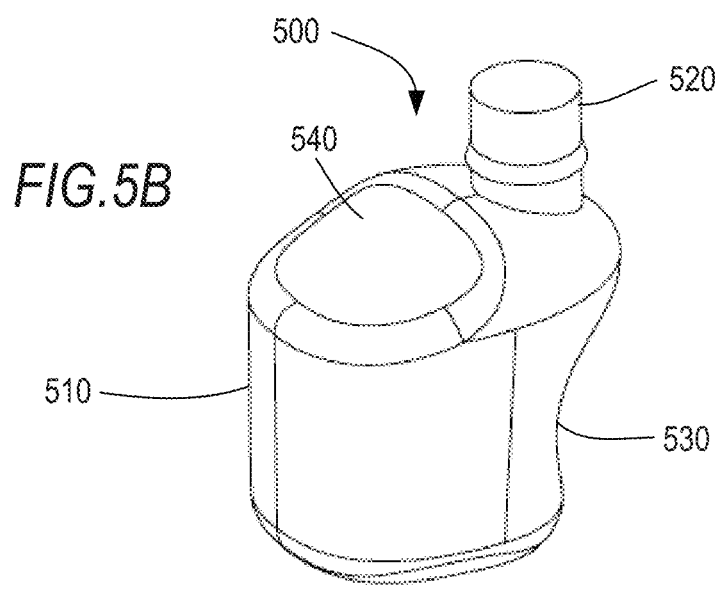
Figure 6:
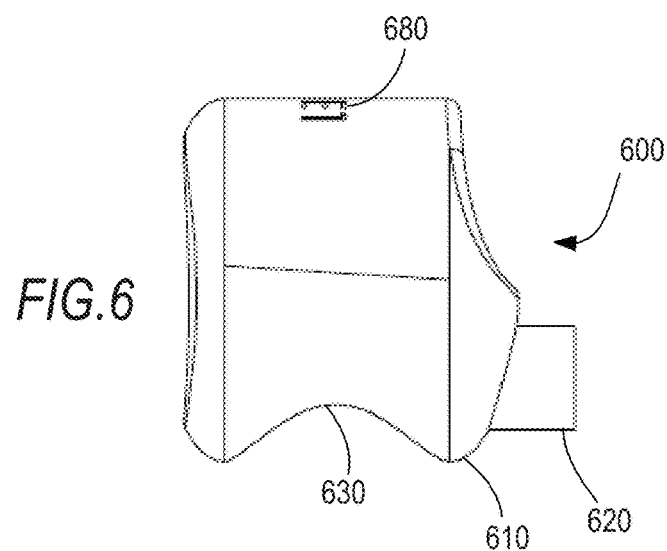
FIG. 6 is a side view of an exemplary dispensing device, in accordance with various embodiments of the present invention.
Figures 7A, 7B:
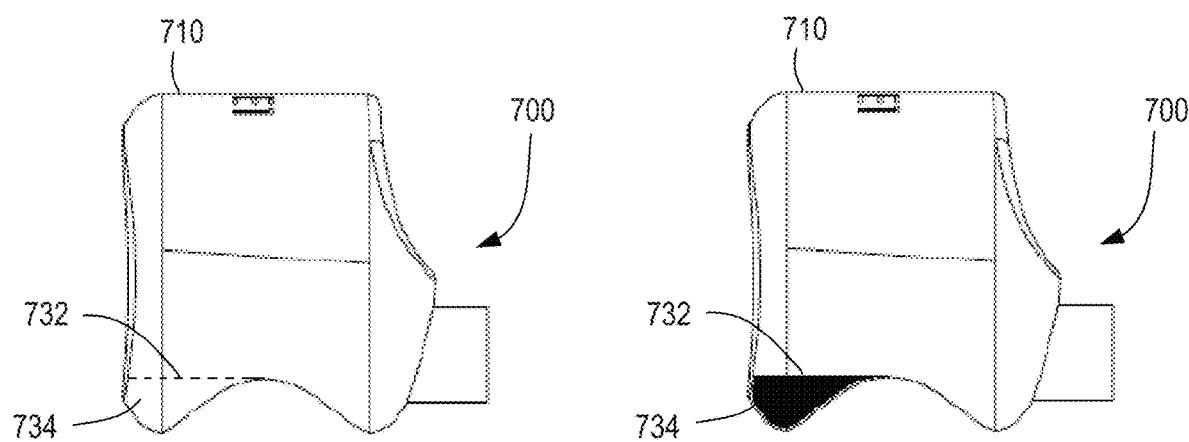
FIGS. 7A and 7B are side views of an exemplary dispensing device, similar to the device of FIG. 6, having an internal wall structure, in accordance with various embodiments of the present invention.

In some dispensing device embodiments, it is recognized that, depending on how the device is oriented prior to being positioned over a user's anatomical structure for drop dispensing, some of the drops in the device can become temporarily trapped in the internal end of the concave channel proximate the bottom of the container body (i.e., the bottom concave end). See, e.g., dispensing devices 100, 300, and 600 of FIGS. 1, 3A-3F, and 6. This could potentially lead to waste of often expensive drops (such as those for treating glaucoma). Thus, in certain embodiments, the concavity of the channel can be made smaller, which can allow the drops to more easily flow toward the nozzle for dispensing, even when positioned over a user's nose bridge in a sideways orientation. Dispensing device embodiments having channels with smaller concave angles are shown, for example, in FIGS. 5A and 5B. Dispensing device 500 may be similar to any of the aforementioned dispensing devices, and can include a container body 510, a nozzle 520, a channel 530, and grip areas 540 and 550. In other embodiments, dispensing devices having channels with larger concave angles can additionally include one or more internal wall structures configured to block off the entrance to the bottom concave end. FIGS. 7A and 7B are side views of a dispensing device 700, which may be similar to any of the aforementioned dispensing devices. Dispensing device 700 can include a wall structure 732 disposed internally in container body 710. Wall structure 732 can be composed of any suitable material, and can be constructed to have minimal or no impact to overall compressibility of the dispensing device. The walled or blocked off area 734 can be hollow (e.g., as shown in FIG. 7A) or filled with any suitable material (e.g., as shown in FIG. 7B). In this construction, the drops can flow over the wall structure(s) toward the nozzle in a manner similar to how drops can flow in the dispensing device embodiments shown in, for example, FIGS. 5A and 5B. It is to be appreciated, however, that this is not to say that dispensing device embodiments having channels with larger concave angles (such as those shown in FIGS. 1, 3A-3F, and 6, for example) are deficient or inferior to those having smaller ones. Indeed, those skilled in the art will also recognize that, for any given dispensing device embodiment having any concave angle, drops that may be temporarily trapped at the bottom concave end of the container body can easily be recovered by reorienting the body (such as by shaking or tilting the body). Moreover, it will also be recognized that the aforementioned issue of entrapment may be more pronounced only when the user chooses to apply the channel to the nose bridge, rather than the eyebrow ridge, since the gravitational pull on the drops when the dispensing device is positioned over the eyebrow ridge can prevent them from remaining in the bottom concave end.

Figure 8A:
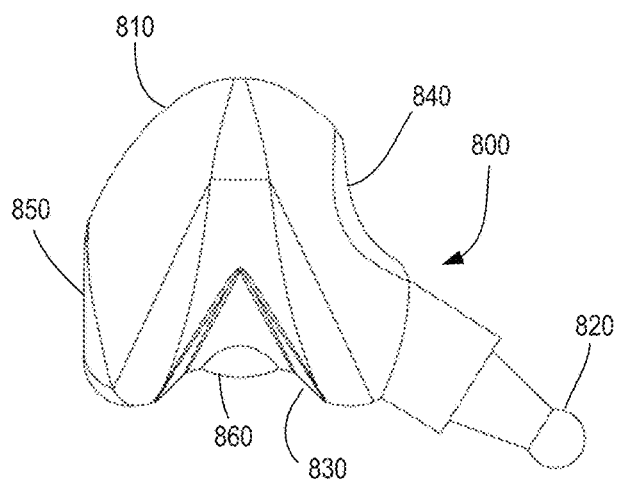
FIGS. 8A-8C are various views of an exemplary dispensing device, in accordance with various embodiments of the present invention.
Figure 8B:
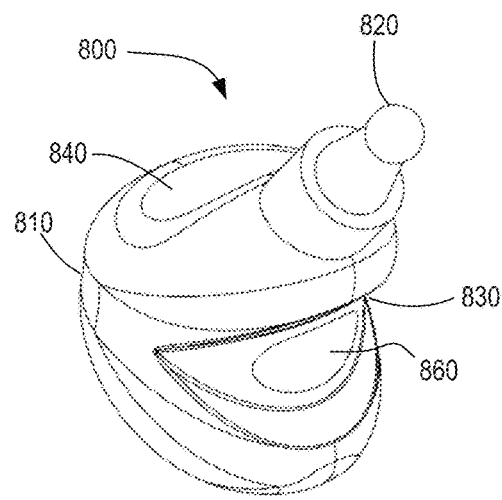
Figure 8C:
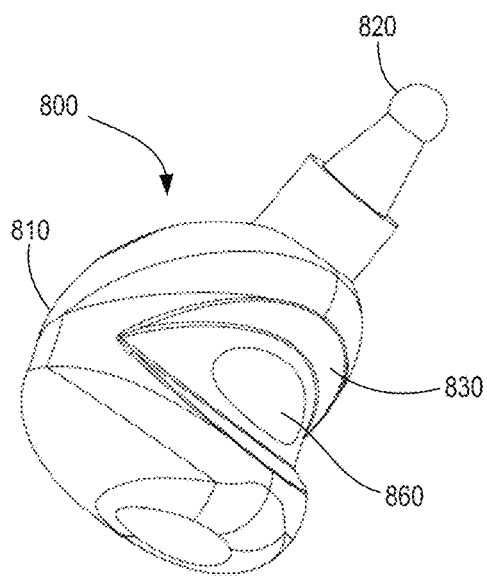

In certain embodiments, the dispensing device's container body can include a protrusion or bulb in the channel. FIGS. 8A-8C are various views of a dispensing device 800 (which may be similar to any of the aforementioned dispensing device embodiments, and which can include a container body 810, a nozzle 820, a channel 830, grip areas 840 and 850, and a protrusion or bulb 860). Depending on the material composition of the container body, force applied to the surface of the container body generally opposite channel 830 can, for example, cause a return force (from a user's nose bridge or eyebrow ridge) to be applied onto protrusion or bulb 860, and provide for a more efficient dispensing of drops (whether in conjunction with force applied to one or more of the grip areas or without the need for or use of the grip areas altogether). Although protrusion or bulb 860 has been described as being configured with a dispensing device constructed as shown in FIGS. 8A-8C, it is to be appreciated that the bulb can be configured with any of the dispensing devices described herein (such as, for example, dispensing devices 100, 200, 300, 500, 600, or 700).

As depicted in the various drawing figures, the nozzle can also assume a variety of shapes and structures, including different neck and outlet end configurations and orientations (such as, e.g., upward pointing or angled nozzle necks and edged or rounded tips). See, e.g., the nozzles of dispensing devices, 100, 200, 300, 500, and 800. In some embodiments, the container body and the nozzle can be constructed as separate components. In this scenario, the container body can, for example, include an opening for receiving and coupling to the nozzle. The nozzle can be coupled to the container body in any suitable manner, including, for example, via a screw-type mechanism, a press-fit mechanism, or the like. In at least one embodiment, the container body and the nozzle can be constructed as a single integrated unit. Moreover, in certain embodiments, the dispensing device can also include a cap or lid configured to cover the nozzle (see, for example, FIG. 1, particularly cap 175).

FIGS. 9A and 9B are various views of a dispensing device 900 (which may be similar to any of the aforementioned dispensing device embodiments, and which can include a container body 910, a nozzle 920, a channel 930, and grip areas 940 and 950). FIG. 9C is a front view of nozzle 920 when disassembled from dispensing device 900. Dispensing device 900 can include a removable cap 975 and a corresponding raised platform 970 configured to accommodate or receive the cap. Cap 975 can generally protect nozzle 920 from foreign substances and retain drops in the dispensing device.

Figure 10:
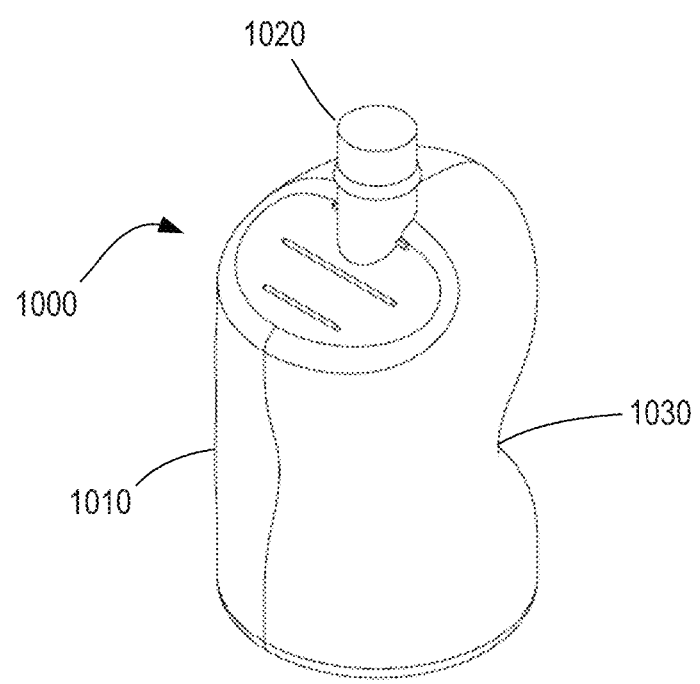
FIG. 10 is a perspective view of an exemplary dispensing device, in accordance with various embodiments of the present invention.

The nozzle can be located at any suitable position on the container body. In certain dispensing device embodiments, the nozzle can be disposed proximate the center of the top portion of the container body (e.g., dispensing device 1000 of FIG. 10, which may be similar to any of the aforementioned dispensing devices, and which can include a container body 1010, a channel 1030, and a nozzle 1020 disposed proximate the center of the top portion of the body). In other embodiments, the nozzle can be disposed at a distance away from the center of the top portion, particularly in an area of the top portion above the channel (e.g., dispensing devices 100, 300, and 500).

In some embodiments, the visual appearance (e.g., color, surface texture, etc.) of the nozzle can be different from the remainder of the container body. This can provide contrast, which can allow a user to better judge the distance of the nozzle from the eye and to generally position the dispensing device for drop dispensing.

In at least one embodiment, the tip of the nozzle can be rounded (e.g., bulbous) or otherwise ball-shaped (e.g., dispensing device 800), which can advantageously guide or allow drops to dispense therefrom in a generally downward direction, and can also prevent some injuries due to the absence of sharp edges at the tip of the nozzle.

In various embodiments, the dispensing device can also include a surface on the container body configured to receive one or more indicia, such as product labels. In preferred embodiments, the indicia-receiving surface can be generally "flat", which can allow the indicia to be applied over the container body and observed without distortion (see, e.g., dispensing devices 500 and 600, particularly label 680 of device 600).

It should be appreciated that the dispensing devices disclosed herein can be utilized to store and dispense any suitable drops. For example, the devices can be configured to store and dispense suspension-type solutions (which may require shaking of the device prior to use) or otherwise.

Figure 11:
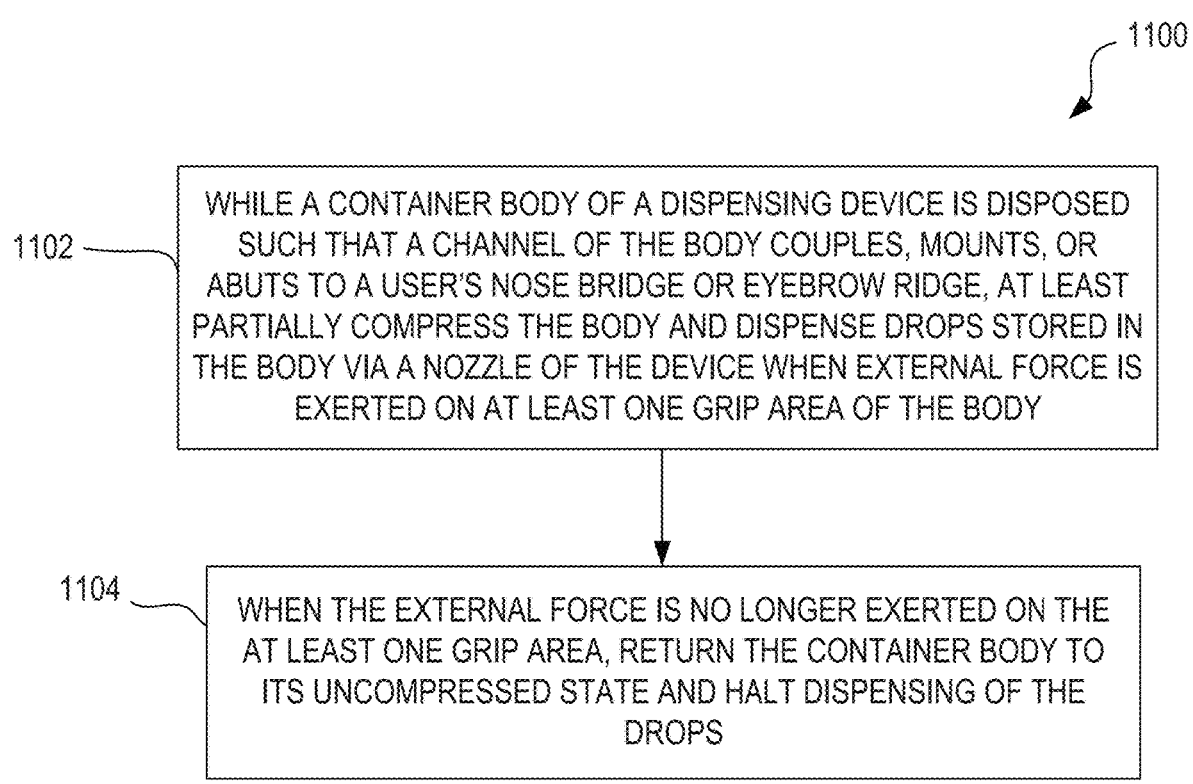
FIG. 11 is a flowchart of an exemplary process for dispensing eye drops from a dispensing device, in accordance with various embodiments of the present invention.

FIG. 11 is a flowchart of an exemplary method 1100 of dispensing eye drops from a dispensing device. The dispensing device can include a container body (e.g., container body 310) configured to store drops, and can have a nozzle (e.g., nozzle 320) coupled to the container body, and a channel (e.g., channel 330) and at least one grip area (e.g., grip areas 340 and/or 350) defined on the container body. At step 1102, while the container body is disposed such that the channel couples, mounts, or abuts to a user's nose bridge or eyebrow ridge, the method can include at least partially compressing the container body and dispensing the drops via the nozzle when external force is exerted on the at least one grip area. For example, while container body 310 of dispensing device 300 is disposed such that channel 330 couples, mounts, or abuts to a user's nose bridge or eyebrow ridge, the method can include at least partially compressing the container body and dispensing the drops via nozzle 320 when external force is exerted on grip areas 340 and/or 350.

At step 1104, when the external force is no longer exerted on the at least one grip area, the method can include returning the container body to its uncompressed state and halting dispensing of the drops. For example, when the external force is no longer exerted on grip areas 340 and/or 350, the method can include returning container body 310 to its uncompressed state and halting dispensing of the drops.

Accordingly, the present invention provides devices and methods for dispensing eye drops, and more particularly, improved containers for facilitating application of eye drops that are ergonomic and that eliminate the need for extraneous gadgets or facilitating devices that may add additional expense to users. The improved devices also advantageously promote patient adherence, which is often a challenge for physicians, especially in dealing with patients suffering from certain conditions, such as glaucoma.

It is to be appreciated that any dimensions, expressed or implied, in the drawings are disclosed for exemplary purposes, and thus some embodiments within the scope of the drawings and this disclosure can exhibit such exemplary dimensions and some may not. While the drawings are not necessarily made to scale, various embodiments within the scope of the drawings and this disclosure can be made with regard to relative dimensions in the drawings.

It will thus be seen that the aspects, features and advantages made apparent from the foregoing are efficiently attained and, since certain changes may be made without departing from the spirit and scope of the invention, it is intended that all matter contained herein shall be interpreted as illustrative and not in a limiting sense.

It is also to be understood that the following claims are intended to cover all of the generic and specific features of the invention herein described and all statements of the scope of the invention that, as a matter of language, might be said to fall therebetween.

What is claimed is:
1. An eye drop dispensing device, comprising:
   a compressible container body configured to store eye drops;
   a nozzle coupled to the container body and configured to dispense the eye drops;
   at least one channel defined on a surface of the container body and configured to at least one of couple, mount, or abut to an anatomical structure of a user, wherein the at least one channel is formed in the sidewall of the container body itself; and
   at least one grip area defined on the container body and configured to compress, when an external force is applied thereto in a direction parallel to the nozzle, and cause at least a portion of the eye drops to dispense via the nozzle,
   wherein the eye drop dispensing device is a single integrated unit with no extraneous protruding structures.

2. The dispensing device of claim 1, wherein the anatomical structure comprises one of a nose bridge and an eyebrow ridge.

3. The dispensing device of claim 1, wherein the at least one channel is defined on a surface of the container body adjacent to the nozzle.

4. The dispensing device of claim 3, wherein the at least one channel is concave.

5. The dispensing device of claim 4, wherein the at least one channel is concave with an angle greater than 180 degrees, an outer surface of the at least one channel being sized to accommodate a nose bridge or an eyebrow ridge.

6. The dispensing device of claim 4, wherein the at least one channel is concave with a curvature modeled by an imaginary circle having a diameter in the range from about 0.5 to 1 inch.

7. The dispensing device of claim 4, wherein the at least one channel is concave, so as to form top and bottom concave ends in the container body, the dispensing device further comprising at least one internal wall structure configured to block off at least a portion of the bottom concave end.

8. The dispensing device of claim 7, wherein the blocked off portion of the bottom concave end is one of hollow and filled.

9. The dispensing device of claim 1, wherein the at least one grip area is further configured to receive one or more fingers of the user.

10. The dispensing device of claim 9, wherein the at least one grip area has a surface with at least one of indentations, depressions and grooves to create additional friction.

11. The dispensing device of claim 1, wherein the nozzle is disposed away from the center of a top portion of the container body, and adjacent to the at least one channel.

12. The dispensing device of claim 1, wherein the nozzle is disposed at the center of a top portion of the container body.

13. The dispensing device of claim 1 further comprising a bulb disposed in the at least one channel.

14. The dispensing device of claim 13, wherein the bulb is configured to receive force from the anatomical structure when the channel couples, mounts, or abuts to the anatomical structure, and to utilize the force to assist in dispensing of the eye drops.

15. The dispensing device of claim 1, wherein the container body is composed of plastic.

16. The dispensing device of claim 15, wherein the plastic comprises at least one of synthetic resins, acrylic, doped acrylic, polyacrylic, or elastomers.

17. The dispensing device of claim 1, wherein the container body is defined to store 1 milliliter to 30 milliliters of eye drops.

18. An eye drop dispensing device, comprising:
- a compressible container body configured to store eye drops;
- a nozzle coupled to the container body and configured to dispense the eye drops, the nozzle being disposed away from the center of a top portion of the container body;
- at least one channel defined on a surface of the container body adjacent to the nozzle and configured to at least one of couple, mount, or abut to any of a nose bridge and an eyebrow ridge of a user, the at least one channel being concave with an angle greater than 180 degrees, an outer surface of the at least one channel being sized to accommodate the nose bridge or the eyebrow ridge, wherein the at least one channel is formed in the sidewall of the container body itself;
- a first grip area defined on the top portion of the container body adjacent the nozzle; and
- a second grip area defined on a bottom portion of the container body, each of the first and second grip areas being configured to receive one or more fingers of the user, the first and second grip areas being configured to compress, when external force is applied thereto in a direction parallel to the nozzle, and cause at least a portion of the eye drops to dispense via the nozzle,
- wherein the eye drop dispensing device is a single integrated unit with no extraneous components and no protruding structures other than the nozzle.

* * * * *